United States Patent [19]

Boblitz

[11] 4,057,401

[45] Nov. 8, 1977

[54] METHANE GAS PROCESS AND APPARATUS

[75] Inventor: Oliver W. Boblitz, Basye, Va.

[73] Assignee: Bio-Gas Corporation, Washington, D.C.

[21] Appl. No.: 720,257

[22] Filed: Sept. 3, 1976

[51] Int. Cl.² .............................................. C02C 1/14
[52] U.S. Cl. .................................. 48/111; 48/197 A; 71/10; 126/270; 195/27; 195/144; 210/2; 210/12; 210/180
[58] Field of Search .................. 48/197 A, 209, 61, 89, 48/111; 71/10; 195/27, 144; 210/2, 12, 14, 96 R, 180, 187; 126/270, 271

[56] References Cited

U.S. PATENT DOCUMENTS

| 1,396,397 | 11/1921 | Borst | 210/12 |
|---|---|---|---|
| 1,929,179 | 10/1933 | Piatt | 210/187 |
| 1,963,581 | 6/1934 | Heukelekian | 71/10 |
| 2,572,767 | 10/1951 | Schlenz | 210/12 |
| 2,661,332 | 12/1953 | Mortenson | 210/2 |
| 3,338,826 | 8/1967 | Kramer | 210/12 |
| 3,875,925 | 4/1975 | Johnston | 126/270 |
| 3,933,628 | 1/1976 | Varani | 210/12 |

OTHER PUBLICATIONS

"Sludge Heating Methods", Greene, 24th Annual Conference, Michigan, Sewage Works Association May 23–25, 1949.
"Digester Problems", Yenchko, Water and Sewage Works 12-1954, pp. 559, 560.

Primary Examiner—Robert L. Lindsay, Jr.
Assistant Examiner—Peter F. Kratz
Attorney, Agent, or Firm—Carroll F. Palmer

[57] ABSTRACT

Apparatus for manufacture of methane gas from sewage sludge or other organic waste comprises a digester tank system, a solar heating unit and conduit means to use hot air from the solar heater to heat the digester tanks. The new methane gas manufacture methods provided by the apparatus operate with water slurries of organic waste at a temperature of about 100° – 140° F to produce about 11 cu. ft. of gas per pound of organic waste and a dewatered residue that may be used as fertilizer.

5 Claims, 4 Drawing Figures

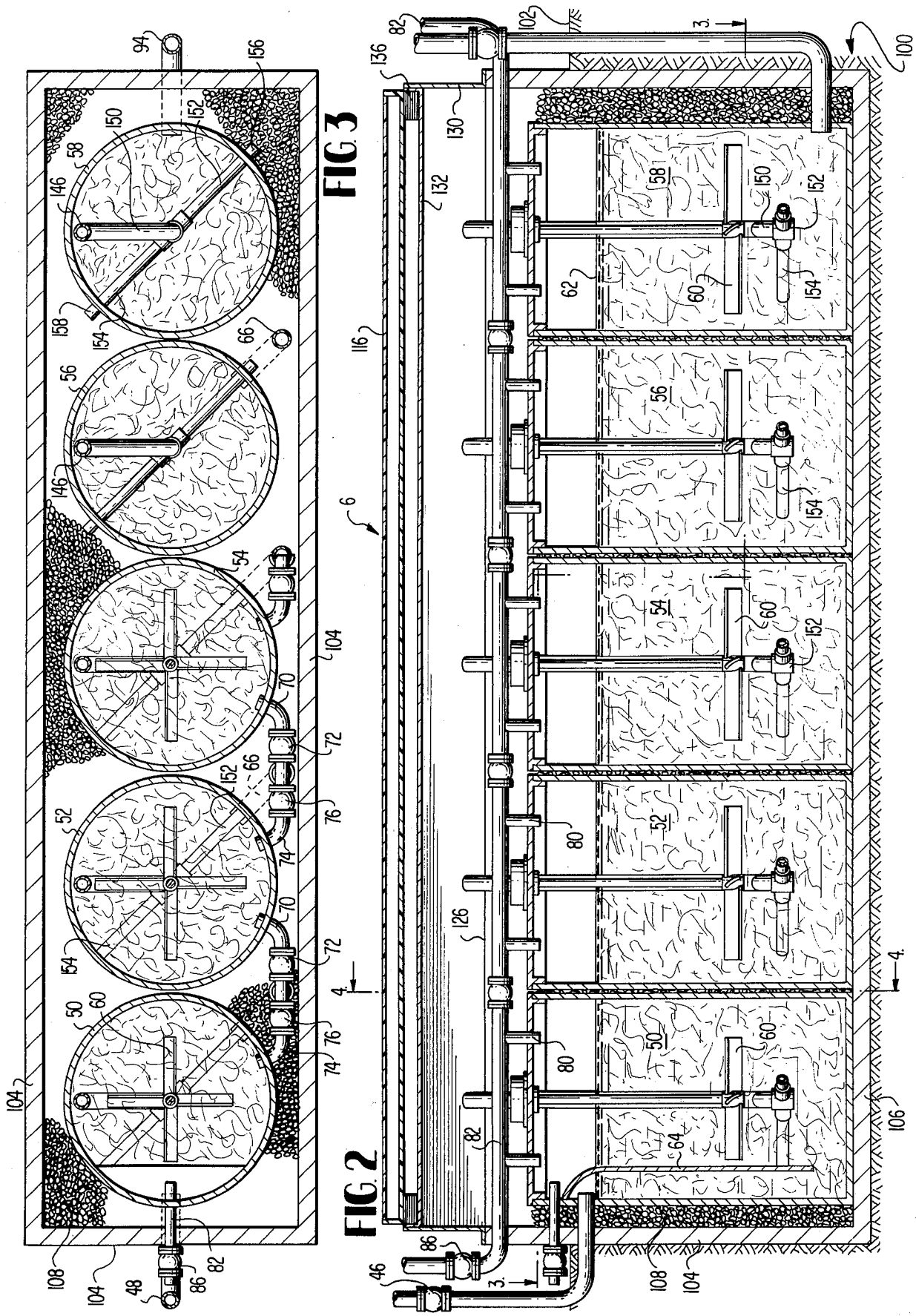

METHANE GAS PROCESS AND APPARATUS

BACKGROUND OF THE INVENTION

1. Field of the Invention

This invention relates to methods and apparatus for the manufacture of methane gas. More particularly, it concerns the utilization of sewage sludge or other organic wastes as a source material for methane gas plus fertilizer and the use of solar heating to reduce the cost of production of the methane gas.

2. Description of the Prior Art

It is well known that methane gas can be generated by bacterial decomposition of organic materials. Because it is produced in nature in this manner in large amounts, particularly in swampy areas, it is commonly called marsh gas. This natural process has recently created some serious problems in suburban residential areas located over or adjacent to trash landfills which are beginning or decay on a massive scale and produce dangerous quantities of methane gas (see "Washington Post", Apr. 4, 1976, p. 1, article entitled "Methane: Richmond's Peril").

The United States generates millions of pounds of trash and organic waste daily, much of which is continued to be disposed of in so-called sanitary landfills. The disposal of such waste and a potent source of valuable energy could be obtained if the bacterial decomposition of organic waste to produce methane gas could be preformed in a controlled manner which would be economically acceptable.

One of the problems in producing methane gas via bacterial action is the heating of large quantities of material to promote bacterial decomposition. Of course, solar energy offers an opportunity for cheap heat and many systems have been devised in an attempt to utilize solar energy for various heating purposes. The following U.S. Patents are representative of disclosures of such systems: U.S. Pat. Nos. 1,753,227; 2,933,885; 1,933,213; 3,048,375.

Notwithstanding the great amount of study and work devoted to solar energy heating and utilization, solar heating has not been extensively used as a major source of reaction heat in conducting continuous chemical processes because of its intermittent availability as well as the high cost of construction and operation of many of the known type of solar heating devices. The production of methane gas together with a desireable way to dispose of organic waste would be promoted if solar energy could be utilized in a practical manner on a commercial scale for the bacterial decomposition of organic waste into methane gas.

OBJECTS

A principal object of this invention is the provision of new methods for the manufacture of methane gas from sewage sludge or other organic waste.

Further objects include the provision of:

1. New apparatus for production of methane gas from organic waste.
2. A continuous, recycling process for production of methane gas from organic waste with the simultaneous production of solid residue useable as fertilizer.
3. A new type of solar heat collectors.
4. A new procedure for the disposal of sewage sludge and other organic waste by municipalities with the simultaneous generation of a source of large amounts of fuel gas and fertilizer.
5. A methane gas production method that weds the energy of the sun to methane producing bacteria to create the desired temperature for maximum production of methane gas and fertilizer.

Other objects and further scope of applicability of the present invention will become apparent from the detailed description given hereinafter; it should be understood, however, that the detailed description, while indicating preferred embodiments of the invention, is given by way of illustration only, since various changes and modifications within the spirit and scope of the invention will become apparent to those skilled in the art from this detailed description.

SUMMARY OF THE INVENTION

These objects are accomplished in part in accordance with the present invention by a method for the manufacture of methane gas which basically comprises bacterially decomposing sewage sludge or other organic waste in an aqueous slurry at a PH of about 6 to 8, heating the slurry for periods up to 10 days to a temperature between 100° and 140° F in major part by indirect heat exchange with hot air produced in a solar energy heater, collecting methane gas produced by bacterial action on the heated slurry, withdrawing portions of the slurry as the process proceeds, dewatering such withdrawn portions and recovering the dewatered solid residue for use as fertilizer.

The objects are further accomplished using new methane gas manufacturing apparatus which basically comprises.

A. a series of digester tanks,
B. a substantially air-tight enclosure surrounding the tanks,
C. a solar heater to heat a stream of air,
D. conduit means to recycle air through the solar heater from the tank enclosure and return it to the enclosure in heated condition and,
E. plumbing to pass organic waste slurry in, through and out the digester tank system.

BRIEF DESCRIPTION OF THE DRAWINGS

A more complete understanding of the new methods and apparatus of the invention may be obtained by reference to the accompanying drawings in which:

FIG. 2 is a fragmentary vertical sectional view of the digester section of the plant shown in FIG. 1.

FIG. 3 is a horizontal sectional view taken on the line 3—3 of FIG. 2.

DESCRIPTION OF PREFERRED EMBODIMENTS

Figure 1:
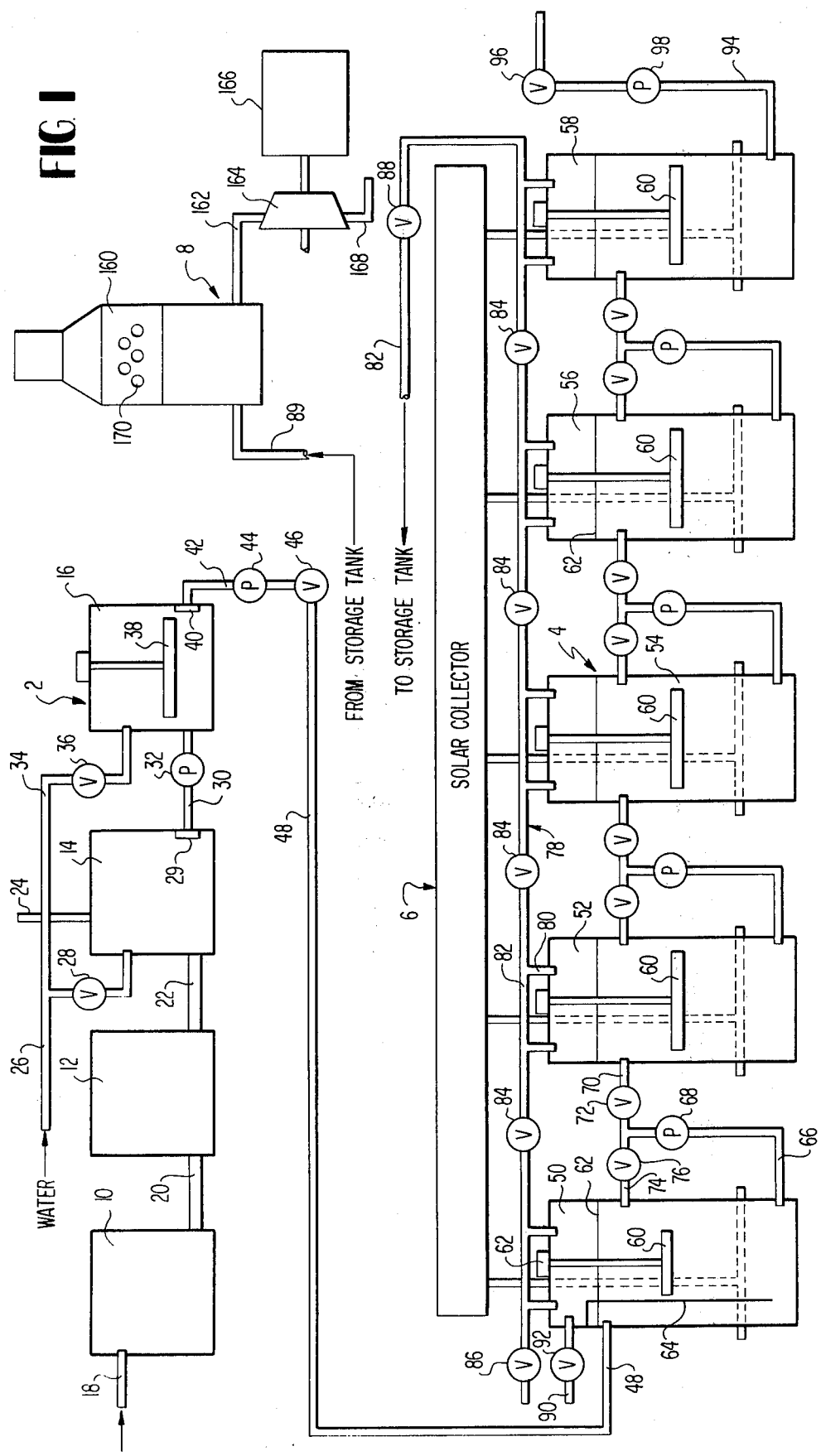
FIG. 1 is a diagrammatic plan view of a plant to produce methane gas and fertilizer in accordance with the present invention.

Referring in detail to the drawings, the gas production plant comprises a feed preparation section 2, a digester section 4, a solar heat section 6 and a gas utilization section 8.

The feed preparation section 2 comprises separation unit 10, shredder unit 12, hydraulic preparation unit 14 and mixer unit 16. A conveyor 18 serves to load organic waste in the separator unit 10. Various types of organic waste may be used as feed stock for the plant, e.g., sewage sludge, waste paper, household trash and garbage or the like. Hence, the form of the conveyor 18 that is used will depend on the form of organic waste being fed to the plant. In fact, it is preferred that separator unit 10 be provided with a variety of conveyors 18 so that the plant may handle several types of feed stocks, e.g., belt conveyers, pneumatic conveyors, liquid conduits and similar available conveyor devices designed to handle waste material.

The separator unit 10 serves to remove large, non-shreddable material from the feed stock, e.g., glass bottles, metal cans, plastic items, etc. The unit 10 may comprise magnetic separators, screen members and similar items known in the art for separating and removing the nonshreddable material and provide a refined feed stock for the shredder unit 12.

The refined feed stock is fed from unit 10 to the shredder unit 12 by conveyor 20. This may be any suitable self-loading conveyor, pneumatic loader, liquid conduit or the like in consideration, as previously indicated, of the particular type of waste being handled. In the shredder unit 12, the refined feed stock is shredded so that it may be readily converted by admixture with water into a slurry, e.g., a particle size to pass a 0.5 inch standard sieve and preferably, to pass a No. 3 sieve.

Conveyor 22 passes the shredded waste, from unit 12 to unit 14. Alternatively, with a feed stock of relatively constant composition not requiring shredding, e.g., sewage sludge, units 10 and 12 can be by-passed and the sludge can be charged directly to unit 14 through charge line 24. In the hydraulic preparation unit 14, the subdivided waste material is mixed with water supplied through line 26 and valve 28 to form a slurry of desired consistency, e.g., 1 to 50 weight percent solids and preferably 5 to 20%.

The mixture formed in unit 14 is fed through screen 29 by line 30 and pump 32 into the mixer unit 16. Here, additional water may be added via line 34 and valve 36. The waste and water mixture in unit 16 is subjected to vigorous stirring by agitator 38, e.g., a worm screwstirrer, so as to form a uniform slurry. The pH of the slurry is monitored and acid or base, e.g., HCl, $CaCO_3$, $NaHCO_3$, etc., is added to adjust the pH to the desired level between 6 and 8, preferably 6.5 to 7.6. The slurry generated in mixer unit 16 is passed through screen 40 to the digester section via line 42, pump 44, valve 46 and line 48 for gas generation as described herein after.

The digester section 4 comprises digester tanks 50, 52, 54, 56 and 58. The tanks are each provided with agitators 60 which may be of any desired type, e.g., worm screw, propeller, etc. powered by motors 62. The tanks are filled each to about 80% of capacity so as to give a slurry top level 62. The slurry for tank 50 comes from mixer unit 16 via line 48. A baffle 64 in tank 50 directs new slurry entering the digester section 4 toward the bottom of tank 50 before it mixes with slurry directly undergoing bacterial reaction.

Each of tanks 50, 52, 54 and 56 has a bottom outlet line 66, pump 68, forwarding line 70 with its valve 72, and recycle line 74 with its valve 76. Line 70 leads slurry from one tank in the digester system to the next tank in the series. Recycle line 74 moves cool slurry from the bottom of a digester tank to the warmer top of the tank to keep an even tempratrue throughout the tank contents. The recycle lines further serve to assist the agitators 60 to keep the waste material in uniform suspension and increases methane production as well as reducing tank retention time. Valves 72 control flow of material from a prior tank into the next, while valves 76 control the degree of recycle within any tank.

The digester system includes methane gas collector means 78 comprising riser pipes 80 atop each digester tank which connect with the collector pipe 82. Valves 84 are provided in the pipe 82 between each of the digestor tanks. They are used for closing pipe 82 between tanks when necessary, e.g., when pumping out a tank for cleaning, refill or the like. Flow of methane gas from line 82 is controlled by valves 86 and 88. Valve 86 is used to regulate transfer of gas from the digester system to storage tanks (not shown) via a gas processing unit (not shown). Valve 88 regulates flow of gas to the gas utilization section 8.

A digester system 4 of the invention basically consists of five tanks operated so that the contents of each tank are changed every 2 days with the plant operating on a ten day cycle. Larger plants advantageously will use multiples of the basic five tank system, e.g., ten tanks distributed in two five tank series. The ten tank plant can be operated so one row of tanks changes every two days and the other row the alternate days for the ten day cycle.

Tank 50 is provided with pipe 90 and valve 92 which are used to sample and test methane gas produced by the plant.

Tank 58 has an outlet pipe 94 controlled by valve 96. Using pump 98, tank 58 is emptied every other day. The effluent through pipe 94 goes to a dewatering unit (not shown) where water is decanted or filtered from the solid residue. The resulting water can be led to sewer or treated for reuse. The residue solids are suitable for drying and use as fertilizer.

The tanks 50-58 may be mounted or supported in any suitable fashion. Preferably, however the tanks are contained in a chamber 100, a major portion of which is located below ground level 102. The walls 104 of chamber 100 can be advantageously formed of cement block or reinforced concrete provided with a parge coat and several coats of pitch on both inside and outside. The same construction can be used for the chamber floor 106. The space between the tanks 50-58 and walls 104 and between tanks is filled with crushed stone 108 which serves as heat-exchange material.

The solar heat section 6 serves to heat the digestion section 4. It comprises a rectangular container 110 having a bottom 112, sides 114 and a transparent top 116, e.g., a clear panel of glass or plastic. Spaced between the bottom 112 and top 116 and parallel thereto is a black wire screen 118. The chamber 100 is closed at the top 120 by closure means 124 having a bottom 126, angled side 128, complex side 130 and a dished top 132. The rectangular container 110 is hinged to the side 128 by hinge 134 to permit it to move between about 30° and 80° of horizontal. An accordian-pleated member is sealed to the bottom 112 of the container 110 and the dished top 132 of closure means 124. The member 136 enables movement of the container 110 on the hinge 134 while maintaining a closed space condition between the bottom 112 and top 132.

A gas inlet to the container 110 comprises tubular members 138 and 140. Member 140 forms an outlet from the chamber 100 through the closure means 124. Member 138 slides within member 140 so that a fluid-tight passage 142 is provided from tank chamber 100 into the solar heat container 110. The upper end 144 of member 138 is shaped to provide non-turbulent flow of air from chamber 100 into container 110.

A gas outlet from container 110 is provided by pipe 146 and matching hole 147 in the container bottom 112.

Figure 4:
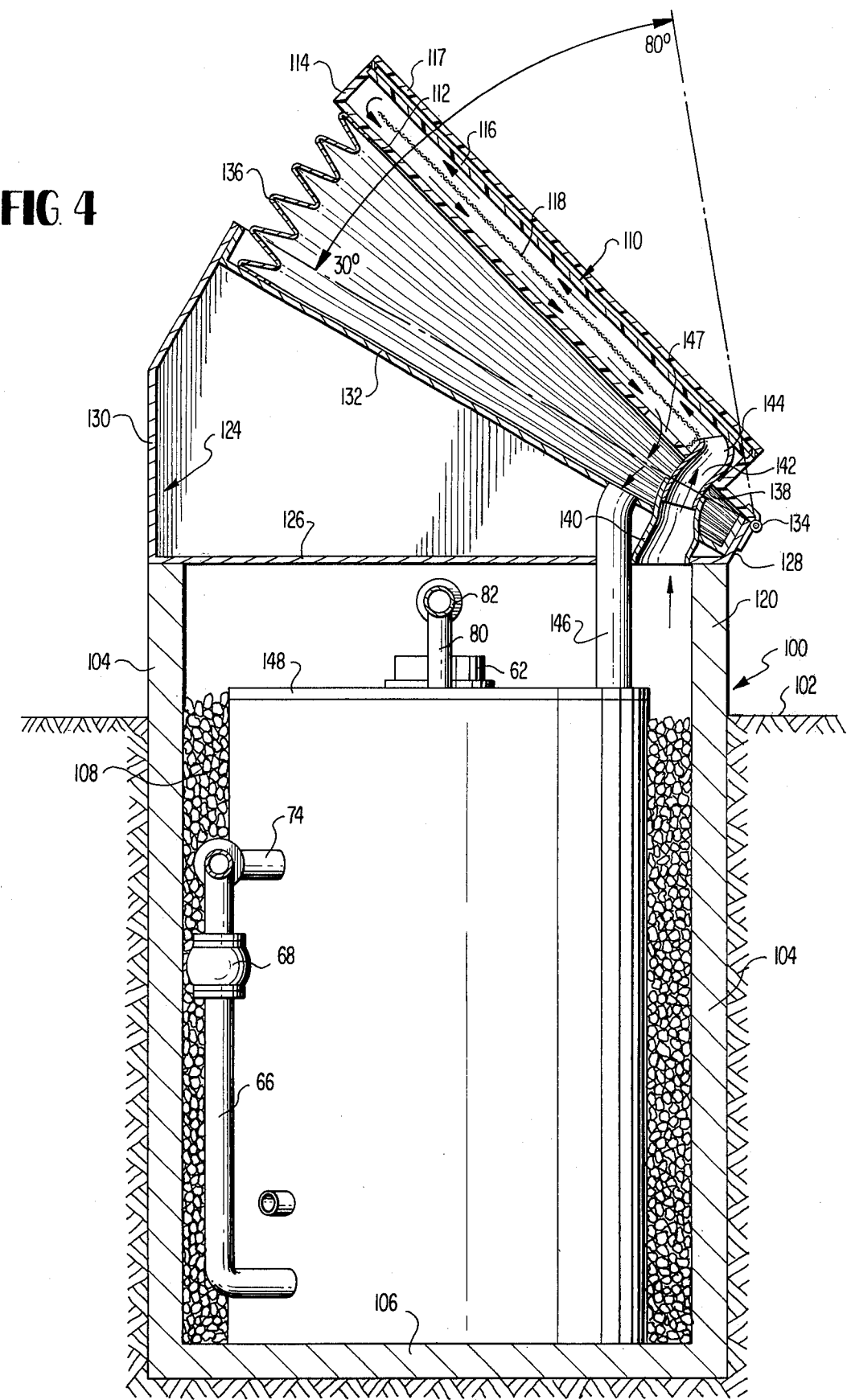
FIG. 4 is a vertical sectional view taken on the line 4—4 of FIG. 2.

The passage of air from chamber 100 via members 138 and 140 through the container 110 and return to the digester system 4 is indicated by the arrows in FIG. 4. The sun radiation passing through clean panel 116 heats the wire mesh 118 which, in turn, heats the air within container 110. As the air flows over the wire mesh 118, above and behind, it becomes highly heated.

The air return pipes 146 pass through the tops 148 of the tanks 50-58 and descend at one side of the tank to below the level of agitators 60. There, the pipes 146 have horizontal portions 150 that join with the central tees 152. These tees 152 divide the heated air flowing from container 110 into two horizontal pipes 152 and 154 which, in turn, exit at ends 156 and 158 respectively into the lower part of chamber 100. Thus, the solar-heated air from heater section 4, frist heats the liquid in the tanks by heat transfer through pipe sections 146, 150, 152 and 154. Second, it heats the tanks indirectly through the tank walls via the heated mass of crushed rock 108.

Blowers (not shown) may be included in lines 146 to provide forced circulation of solar heated air into and out of the digestor section 4. Thermostats, in such case, are used to switch on and off the blowers as required to maintain the temperature in the digester tanks at a desired level between about 100° and 140° F. The angle of the solar heat unit at between about 30° and 80° of horizontal is controlled according to the season of the year and time of day to provide maximum utilization of the solar heat. Methane gas generated by the plant may be taken from the storage tanks (not shown) as required to provide auxiliary heat for operation of the plant.

The gas utilization section 8 permits on-site conversion of some gas produced by the plant into electricity. The boiler 160 is heated by gas supplied through line 82 via valve 88. Steam generated in the boiler is passed by pipe 162 to the engine or turbine which powers the electrical generator 166. Low pressure steam can be exhausted from the turbine 164 through pipe 168 and used to supplement solar heat in heating the digester section 4. Additionally, heat from boiler tubes 170 may be blown into the bottom of the crushed rock storage in chamber 100 to give auxiliary heating.

Any suitable materials may be used for construction of the gas plant components as described. Useful materials have been indicated for some parts, but availability of materials, costs and similar factors will dictate material choices at various locations. By way of example, the wire mesh 118 can be 18 mesh, 16 lb. aluminum screen finished by painting or anodizing in a dull black finish. The use of wire mesh here increases efficiency and provides great weight and cost reduction as compared to the use of a solid metal plate of copper, aluminum or the like.

The methods and equipment as shown and described provide a 10 day continuous process that can extract about 80 percent of the methane from sewage sludge and other organic waste. About 11 cu. ft. of methane gas (STP) can be extracted for each pound of organic solids, equal to about 7,000 to 9,000 BTU's. Most of the digester tank heat, in view of the construction of the equipment, will be obtained by the new solar heat collectors which can be adjusted at right angle to the sun. This new solar heating system can reduce the cost of producing methane gas by about 40 percent. Moreover, the solid waste that is recovered may be sold and used as fertilizer providing additional production cost savings of about 15 percent.

The embodiments of the invention in which an exclusive property or privilege is claimed are defined as follows:

1. Apparatus for the manufacture of methane gas comprising:
    a plurality of digester tanks arranged in series,
    first conduit means connecting said tanks for fluid flow between them, pump means to provide fluid flow through said first conduit means,
    agitator means for mixing liquid material contained within said tanks,
    a substantially air-tight enclosure surrounding said tanks,
    a solar heater to heat a stream of air passing through the heater,
    second conduit means connecting said enclosure with said solar heater for passage of a stream of air from said enclosure to said solar heater,
    third conduit means connecting said solar heater to said enclosure for passing a stream of air heated in said solar heater into said enclosure for indirect heat exchange with liquid material contained within said tanks,
    fourth conduit means connected to said enclosure to remove methane gas produced in said tanks therefrom,
    fifth conduit means connected to the last digester tank in said series to remove liquid material from said last tank, and
    sixth conduit means connected to the first digester tank in said series to introduce liquid material into said first tank.

2. The apparatus of claim 1 wherein said solar heater comprises a rectangular container comprising a bottom and four sides, a transparent panel covering the top of said container, a rectangular section of black wire screen positioned in said container parallel to said transparent panel, a hinge attached to one edge of said container to permit it to be moved between a position of about 30° to 80° of horizontal and an accordian pleated unit attached to the bottom of said container to provide a closed chamber beneath said container which can vary in size as the container is moved between said 30° to 80° positions.

3. In the method of producing methane gas by anaerobic digestion of a slurry of water material at a pH of between about 6 and 8 and a temperature between about 100° to 140° F wherein methane gas produced by bacterial action upon the heated slurry is collected and dewatered solid residue for use as fertilizer is obtained, the improvement which comprises exposing a metal screen to rays of the sun passing through a transparent panel spaced apart from said metal screen forming a first longitudinal passageway therebetween, said panel defining the sunward side of a gas-tight chamber, said chamber having a second longitudinal passageway substantially parallel to said first passageway defined by the shadow side of said metal screen and the spaced-apart back of said chamber, passing air through said first passageway, then through said second passageway, next passing the resulting heated air in indirect heat exchange with slurry undergoing anaerobic digestion and finally recycling said air to said first passageway for continuation of said procedure for heating of the digesting slurry using solar energy.

4. The method of claim 3 wherein heat from combustion of methane gas produced by said method is employed to supplement said hot air heating.

5. The method of claim 3 wherein said organic waste material is sewage sludge.

* * * * *

UNITED STATES PATENT OFFICE
CERTIFICATE OF CORRECTION

PATENT NO. : 4,057,401
DATED : November 8, 1977
INVENTOR(S) : Oliver W. Boblitz

It is certified that error appears in the above-identified patent and that said Letters Patent are hereby corrected as shown below:

First page, in item [73] Assignee: change "Bio-Gas Corporation" to --Bio Gas Systems, Inc.--

Signed and Sealed this

Eleventh Day of April 1978

[SEAL]

Attest:

RUTH C. MASON
Attesting Officer

LUTRELLE F. PARKER
Acting Commissioner of Patents and Trademarks